United States Patent [19]
Larkin

[11] Patent Number: 4,602,910

[45] Date of Patent: Jul. 29, 1986

[54] COMPARTMENTED FLEXIBLE SOLUTION CONTAINER

[76] Inventor: Mark E. Larkin, 419 Northgate, Lindenhurst, Ill. 60046

[21] Appl. No.: 582,250

[22] Filed: Feb. 28, 1984

[51] Int. Cl.[4] .......... A61M 5/00

[52] U.S. Cl. .......... 604/87; 604/410; 604/416

[58] Field of Search .......... 604/410, 416, 87

[56] References Cited

U.S. PATENT DOCUMENTS

| | | | |
|---|---|---|---|
| 2,764,983 | 10/1956 | Barasch et al. | 604/416 |
| 3,257,072 | 6/1966 | Reynolds | 604/410 |
| 3,608,709 | 9/1971 | Pike | 206/47 A |
| 3,674,134 | 7/1972 | Turner | 206/47 A |
| 3,750,907 | 8/1973 | Steele | 222/107 |
| 3,856,138 | 12/1974 | Maekawa et al. | 604/416 |
| 3,964,604 | 6/1976 | Prenntzell | 206/219 |
| 3,985,135 | 10/1976 | Carpenter | 604/410 |
| 4,396,383 | 8/1983 | Hart | 604/416 |
| 4,484,920 | 11/1984 | Kaufman | 604/416 |

FOREIGN PATENT DOCUMENTS 0077189 4/1983 European Pat. Off. .

*Primary Examiner*—John Doll

*Assistant Examiner*—Anthony McFarlane

[57] ABSTRACT

A compartmented and collapsible container system for sterile components which has a separate compartment for each component with a secondary container compartment within a larger container compartment, yet will permit the intermixing of the components upon the selective delamination of a frangible seal which separates the compartments. The compartmented container is specifically constructed for use with two components which are normally incompatible when mixed. The container herein described permits the two incompatible components to be sterilized in a disposable, flexible container. At the time of usage, the two materials can be readily intermixed in the same container and administered therefrom, such as with the usual intravenous administration equipment. An important feature of the container system is a selective frangible seal which seals one container inside the other, yet is readily delaminated to permit the free flow of materials between the container compartments while securing the containers to each other.

14 Claims, 7 Drawing Figures

COMPARTMENTED FLEXIBLE SOLUTION CONTAINER

BACKGROUND OF THE INVENTION

This invention relates to a flexible container for materials which are normally incompatible when mixed together and stored. More particularly, this invention relates to a compartmented container wherein two incompatible materials can be sterilized in the flexible container and can subsequently be readily intermixed and administered in a safe and convenient manner.

Compartmented containers for different types of materials are well known in the art. For example, in U.S. Pat. No. 3,608,709 a laminated package is provided with an intermediate seal which includes a release area to allow the two materials to intermix. In U.S. Pat. No. 3,964,604 a rupturable seam barrier is disclosed in a laminated multi-compartmented container for a similar purpose. U.S. Pat. Nos. 3,674,134 and 3,750,907 also illustrate rupturable seals in multi-layered packages, with U.S. Pat. No. 3,674,134 depicting an intermediate or inhibiting layer between two other layers for delamination purposes and U.S. Pat. No. 3,750,907 illustrates a foil and resin lamination and the use of processing conditions to produce strong and weak seal portions.

The prior art does not provide a multi-compartmented container for internally intermixing an intravenous solution which can be readily sterilized yet activated in a desired manner. In the manufacture of containers in the health care field a primary consideration is the sterility of the contents. In the prior art containers there are inherent deficiencies that either prevent them from being produced economically, fail to be fabricated and function as desired, or neglect to meet all end-user requirements, including sterility.

It is an advantage of the present invention to provide a container separated into two compartments containing two components that would be intermixed at the time of use by means of rupturing an internal frangible member to allow the separated components to completely intermix with each other. Other advantages are a flexible intravenous solution container containing parenteral intravenous products to be intermixed and subsequently administered; a multi-compartmented container having a delaminated seal member separating the compartments wherein the means of rupturing the seal separating the two compartments can be consistently controlled; a multi-compartmented container that is simple in design and able to be mass produced using existing technology, commonly used fabrication equipment and applicable to a wide range of materials; a container which provides a method of intermixing at least two I.V. components, so that when they are combined, maintenance of sterility is assured; and a method of combining two separated components for an admixture solution that is not time consuming, does not require special facilities, or highly trained personnel to activate.

SUMMARY OF THE INVENTION

The foregoing advantages are accomplished and the shortcomings of the prior art are overcome by the compartmented flexible container system for at least two different and unstable-when-mixed fluids, wherein one container is seal within the other, and the fluids can be intermixed inside the outer container through a breaking of a frangible member between the containers. The first container has a body section with spaced apart, opposing, substantially flat walls defining a cavity portion, the walls being formed from plastic resinous material and having internal wall surfaces. The second container body section has spaced apart, opposing, substantially flat walls, and also defines a cavity portion with the walls formed in part from a different material than the plastic resinous material forming the first container body section. The second container body section is positioned within the confines of the first body section and is spaced from at least one wall portion thereof. The second container body section is secured to the internal wall surfaces of the first container, with the walls of the second container secured in part to each other in a selective, delaminated seal member arranged so that internal fluid forces will effect a parting of the sealed second container walls from each other, but not the parting of the second container body section from the internal wall surfaces of the first container. In the preferred embodiment, the first container body section is fabricated from two separate sheets of thermoplastic material which are sealed at the periphery, and the second container walls include a metal foil layer with the delaminated seal positioned away from the periphery of the first container in all directions. In one embodiment, the selective delaminated seal is formed by a partial parting of the second container walls and with a seal at the end of the partial parting. To activate the system, all that is required is that a force be applied to the first container walls outside the second container body section. This will effect a delamination of the delaminable seal, allowing the fluid contents of the first container to flow and mix with the fluid contents of the second container. The first container will have associated with it the usual additive and administration ports to allow the contents of the solution to be administered to a patient.

BRIEF DESCRIPTION OF THE DRAWINGS

A better understanding of the compartmented, flexible container of this invention will be had by reference to the following description, taken together with the accompanying drawings, wherein.

DESCRIPTION OF THE EMBODIMENT

Figure 1:
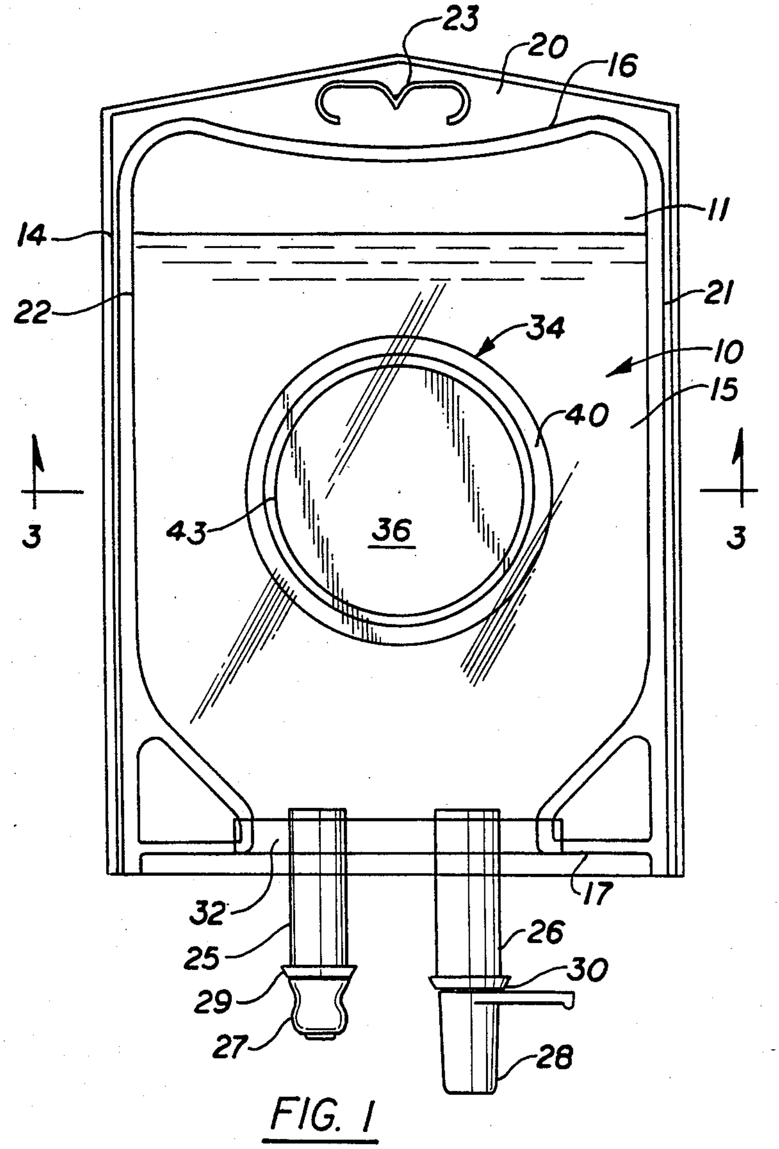
FIG. 1 is a view in front elevation showing the container system of this invention with the second container positioned centrally within the first container.
Figure 7:
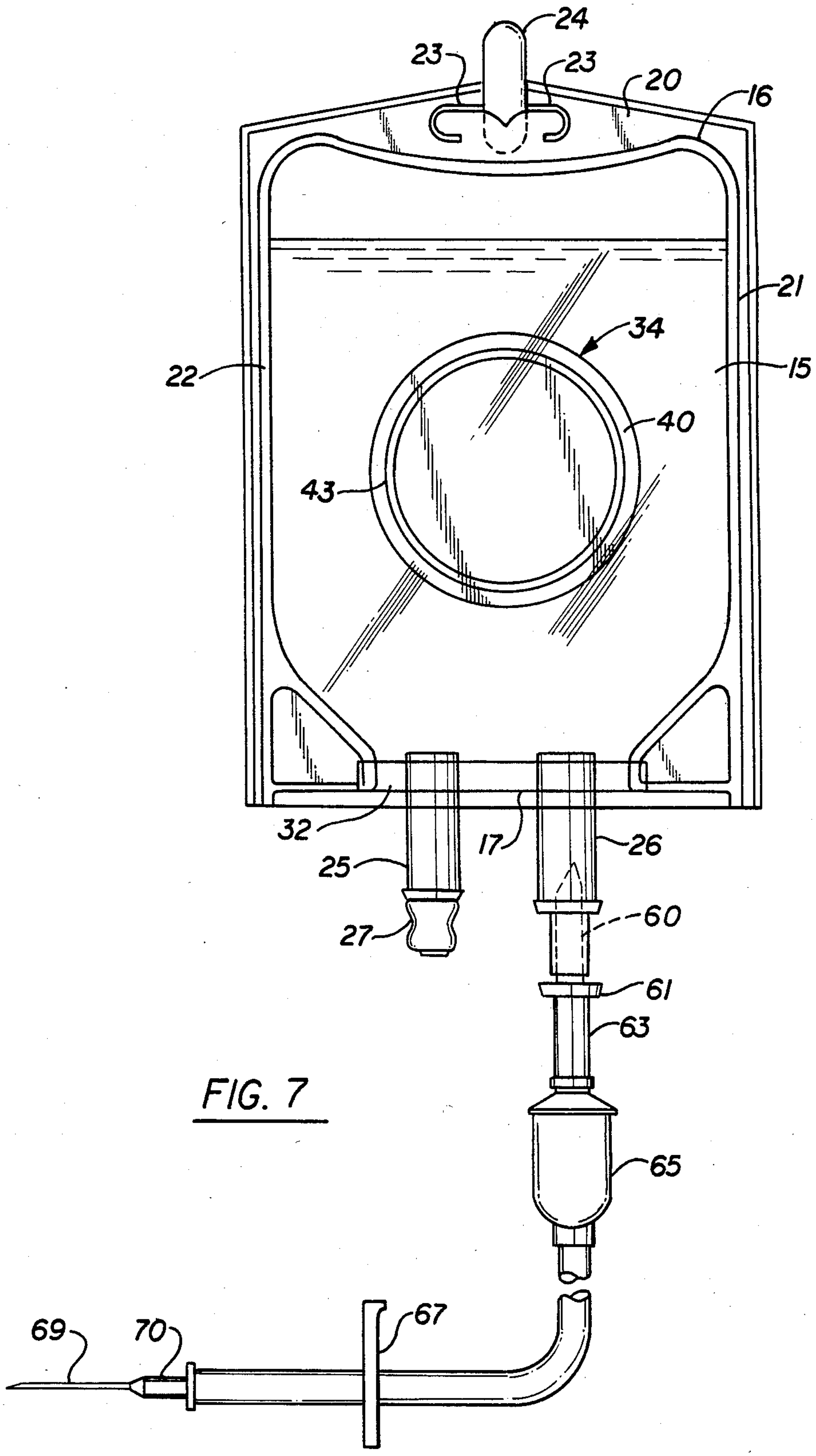
FIG. 7 is a view in front elevation illustrating the container system of FIG. 1 operatively connected to the usual intravenous administration set.

Referring to FIG. 1 of the drawing, the flexible compartmented container generally 10 includes a primary container generally 14 composed of a tubular body section 11 having a front wall 15, which at one end terminates in an end wall 17, and in another end wall 16 at the opposing end. Extending from end wall 16 is hanger section 20 having a tear detail 23 to provide an aperture for the usual supporting hook 24 (see FIG. 7). Extending through end wall 17 and by means of a mandrel-type seal 32, are tubular ports 25 and 26. Tubular port 25 in this instance is an additive port which is sealed closed through reseal cap 27. Tubular port 26 is an administration port which is closed by flanged protective cap 28. Both ports have the usual flanges 29 and 30 for purposes of making connection with caps 27 and 28 by means of inner tubular members (not shown).

Figure 2:
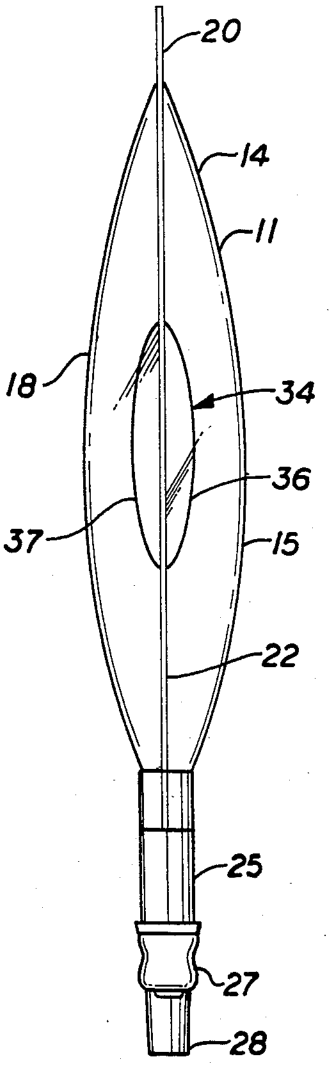
FIG. 2 is a view in side elevation of the container system shown in FIG. 1.
Figure 3:
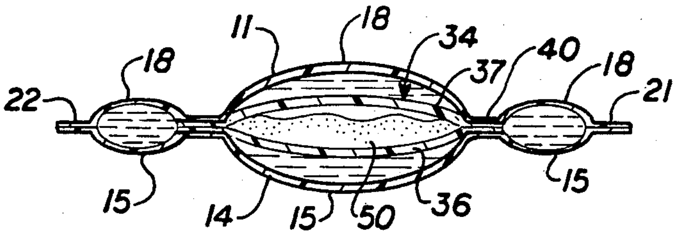
FIG. 3 is a view in horizontal section taken along line 3—3 of FIG. 1.
Figure 4:
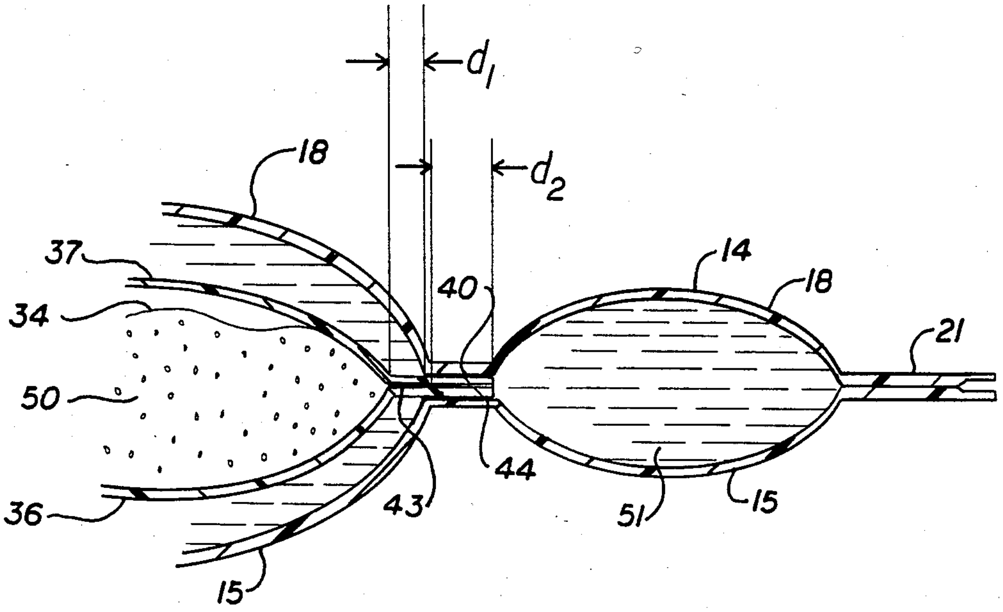
FIG. 4 is an enlarged partial view of the container system shown in the previous FIGURES illustrating the seal portion prior to activation.
Figure 6:
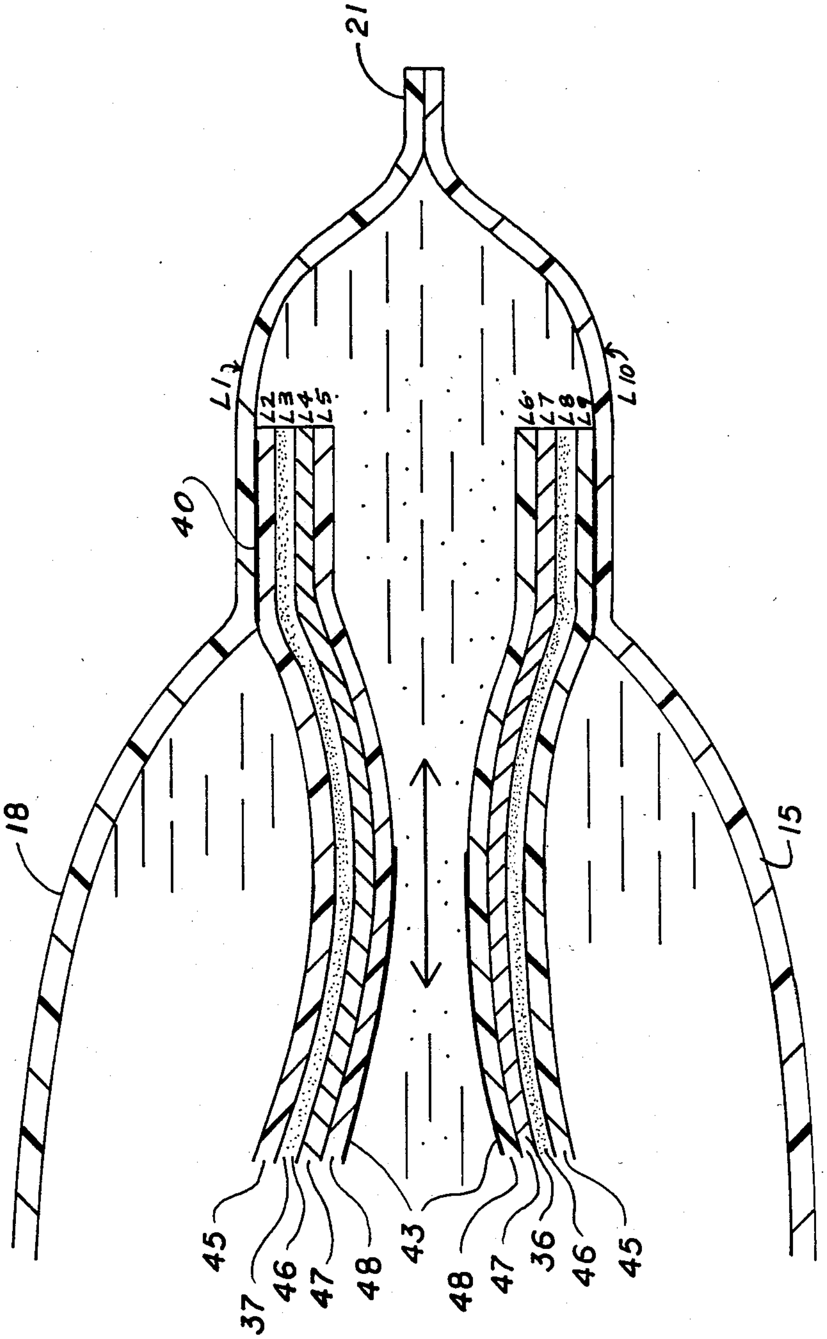
FIG. 6 is an enlarged partial view of the laminated wall structure of the inner or second container in an activated condition as illustrated in FIG. 5 but with the laminated wall structure extending nearer the side wall of the first container.

As best seen in FIGS. 2 and 3, a second container generally 34 is sealed within body section 11 of primary container 14. Secondary container 34 includes walls 37 and 36 which in this instance are formed from a layered material and are sealed in the area 43. The layers of material are best illustrated in FIG. 6 and are described as follows: layers L2 and L9 referred to as numeral 45 is a polyvinylchloride material and is 0.015′ in thickness. Layers L3 and L8 referred to as numeral 46 is an appropriate adhesive material such as a urethane which will effect adherence between layers L2 and L9 and layers L4 and L7, respectively, which are referred to as numeral 47. It will have a thickness of 0.005′. Layers L4 and L7 are composed of aluminum foil and range from 0.0035′ to 0.009′ in thickness. Reference numeral 48 refers to layers L5 and L6 and is a dispersion of polypropylene being approximately 0.0005′ thick. It will be further noted that in the area indicated by the numeral 44 that there is a parting between walls 37 and 36 in fluid communication with the contents of primary container 14 with seal or delaminated area 43 positioned at the end of the partial parting.

Fabrication

The container system of this invention is easily fabricated. In a preferred manner, an antibiotic powdered material 50 will be placed between walls 36 and 37. A sealing device of the heating type will circumferentially seal walls 36 and 37 to each other in seal area 43. The formed second container 34 will then be centered within two sheets of polyvinylchloride thermoplastic material which will form the front and back walls 15 and 18. A sealing device of the heating type which was employed to effect seal 43 will then be utilized to seal walls 15 and 18 to P.V.C. layers 45 composing walls 36 and 37, respectively, in the area indicated by the numeral 40. At the same time, side walls 22 and 21 will be formed by means of heat sealing and the hanger detail 20 with tear detail 23 will also be formed. Subsequently, the two ports 25 and 26 will be mandrel sealed, such as at 32, to be in fluid communication with the inside of primary container 14. Container 14 will be filled with a diluent such as a dextrose solution, through administration port 26. Subsequently, port 26 will be closed such as by a commonly used inner tube with a pierceable diaphragm (not shown) and protective cap 28. The filled container will then be sterilized, such as by autoclave sterilization and then provided with an overwrap to environmentally protect from any external foreign contaminants, moisture loss, gas permeation, etc. If desired, the overwrapping and sterilization could be effected at the same time. Further, depending upon sterilization cycle of each material, if the cycles are different, one component can be filled and sterilized and the other compartment filled and sterilized. Also if desired, liquid diluent 51 could be placed in the secondary container 34 and powder material in the primary container 14. In this instance the volume of secondary container 34 would be proportionately larger with respect to the primary container than shown in FIG. 1.

Operation

Figure 5:
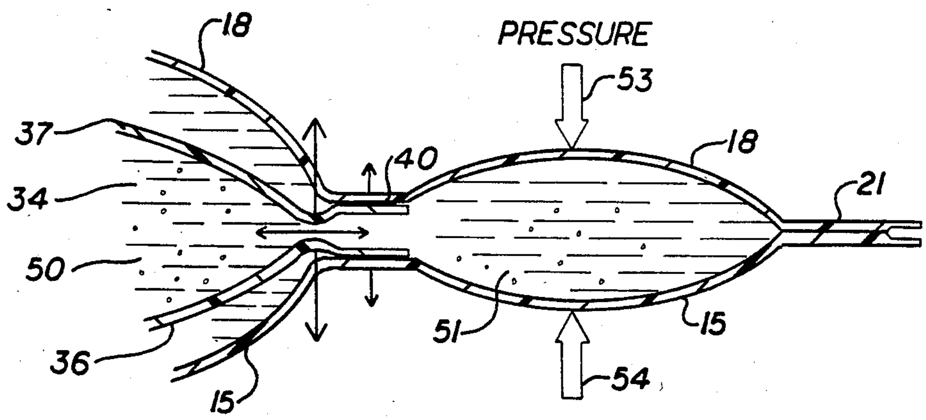
FIG. 5 is a view similar to FIG. 4, illustrating the activation of the container system.

When it is desired to utilize container system 10, the overwrap may be removed and a force imparted to front and back walls 15 and 18 as indicated in FIG. 5 by pressure vectors 53 and 54. This would be effected such as by squeezing with the thumb a forefinger. This pressure will force the diluent 51 in lateral directions to force liquid to enter the sealed area 40 and the parting section 44. The delaminated seal 43 forms a weaker seal, as indicated by lines $d_1$, than the seal between front and back walls 15 and 18 sealed to walls 36 and 37, respectively, of inner container 34 indicated by lines $d_2$ and numeral 40. Accordingly, it will break prior to any breaking of seal between the container walls. It should be pointed out in this instance that a workable seal area is of the following formula:

$$d_2 = d_1 \times 4.$$

After the diluent and antibiotic powder are thoroughly mixed, the mixed solution can be administered by the usual administration set having a piercing pin 60, flange 61 interconnected with tubing 63, a sight chamber 65 and a clamp 67 secured on the tubing. The usual needle 69 will be attached by means of hub 70.

The preferred plastic resinous material or plastic sheet material forming front and back walls 15 and 18 as well as end walls 16 and 17 is polyvinylchloride. However, other thermoplastic, polyolefin materials such as polypropylene, polyethylene or polyester could be employed, depending on the types of materials to be placed in the containers and the sterilization thereof. While one embodiment of a multilayered seal area has been illustrated for use in conjunction with a delaminated seal, other layers of different materials could be utilized. For example, in place of dispersion layer 48 a layer of polypropylene and polyethylene could be substituted. These layers would be secured to foil layers 47 by means of an additional adhesive layer such as 46. The remaining adhesive layers such as 46 between foil layers 47 and P.V.C. layers 45 would be the same as previously described. While aluminum foil is preferred, other types of metal foil could be utilized. The preferred resinous plastic for forming the various tubular ports such as 25 and 26 is a polyolefin. However, other plastic tubing could be utilized, depending on the sealing requirements and compatability with the sheet plastic forming the various body sections of the containers.

While the primary and secondary containers of this invention have been described for use with an antibiotic material and a diluent, other applications for the container are numerous in the related medical field, such as enteral feeding, continuous ambulatory dialysis, chemotherapy, etc. Further, the compartmented container of this invention fulfills the need for a container in industries apart from the medical field, such as food and beverage, cosmetics, adhesives, etc. While the container system of this invention has been described for use with a single delaminable secondary container to form a dual compartment container, it is obvious that several of the secondary container members could be sealed in a primary container to form a multiplicity of compartments, the contents of which can be intermixed by breaking the various delaminated sealable members in any preferred sequence. It should also be pointed out that the term "fluid material" as employed in this specification or claims is meant to imply a medicament or diluent material which will flow from one compartment to another, whether a liquid, solid or gas.

It will thus be seen that through the present invention there is now provided a flexible container system for any mixed unstable materials which is easily fabricated and readily utilized to mix the compartmented materials. The container with the delaminated seal member can be activated with a minimum amount of effort yet provide a container system which will not be activated unintentionally. The container system of this invention can be molded in various configurations to be adapted to numerous types of unstable materials. The materials when placed in the various compartments of the container are readily sterilized and will remain sterile until the desired intermixing. All of the foregoing is accomplished in the container which can be fabricated in a manner which does not result in increased cost and accordingly, in a container system which is disposable.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A compartmented flexible container system for temporarily storing and subsequently intermixing at least two different fluids comprising:

a first container body section having spaced apart opposing substantially flat wall members defining a first cavity portion, said wall members formed from a flexible plastic resinous material and having internal wall surfaces; and a second container body section having spaced apart opposing substantially flat sides defining a second cavity portion, said sides formed from a composite material including a foil layer;

said second container body section positioned within the confines of said first container body section and spaced from at least one wall wall member thereof, said second container body section secured to said internal wall surfaces of said first container body section and said sides of said second container body section secured in part to each other at their perimeters in a selective, delaminated seal member constructed and arranged so that internal fluid forces will effect an opening of said seal member by the separation of the sealed sides one from the other but not parting of the second container body section from the internal wall surfaces of said first container body section;

whereby upon the application of force to said first container body section wall members outside said second container body section, said seal member will open and the contents of said compartments can be intermixed.

2. The compartmented flexible container system as defined in claim 1 wherein said first container body section is fabricated from two separate sheets of thermoplastic materials which are sealed together at their periphery.

3. The compartmented flexible container system as defined in claim 2 wherein said delaminated seal member is positioned away from said periphery of said first container body seetion in all directions.

4. The compartmented flexible container system as defined in claim 1 wherein said foil is a metal foil and wherein said foil in said composite material forming said second container sides is located between layers of thermoplastic resinous material to form in part said delaminated seal member.

5. The compartmented flexible container system as defined in claim 1 wherein said selective delaminated seal is formed by a partial parting of said second container sides so that fluid communication is effective with said first cavity portion of said first container body section prior to delamination.

6. The compartmented flexible container system as defined in claim 5 wherein said second container body section is secured to said internal wall surfaces of said first container body section adjacent said partial parting of said second container sides forming a portion of said delaminated seal.

7. The comoartmented flexible container system as defined in claim 6 wherein said second container body section is secured to said internal wall surfaces of said first container body section with respect to said delaminated seal between said second container body section sides so that said delaminated seal requires approximately one-fourth the force for separation as compared to said securing of said second container body section to said first container body section.

8. The compartmented flexible container system as defined in claim 4 wherein said metal foil is aluminum.

9. The compartmented flexible container system as defined in claim 1 wherein said seal between said first and second container body sections and said delaminated seal are formed using a heat sealing process.

10. A compartmented flexible intravenous container system for temporarily storing and subsequently intermixing at least two different intravenous fluids comprising:

a first container body section having spaced apart opposing substantially flat wall members defining a first cavity portion, said wall members formed from a sterilizable plastic resinous material and having internal wall surfaces; and a second container body section having spaced apart opposing substantially flat sides defining a second cavity portion, said walls formed from a compositie sterilizable material including a foil layer;

said second container body section positioned within the confines of said first container body section and spaced from at least one wall wall member thereof, said second container body section secured to said internal wall srfaces of said first container body section and said sides of said second container body section secured in part to each other at their perimeters in a selective, delaminated seal member constructed and arranged so that internal fluid forces will effect a parting of the sealed second container sides from each other but not the parting of the second container body section from the internal wall surfaces of said first container body section; and an administration port extending from said first container body section in fluid communication with said first cavity portion;

whereby upon the application of force to said first container body section wall members outside said second container body section, said sealed container sides will delaminate and the contents of said compartments can be intermixed.

11. The compartmented flexible intravenous container system as defined in claim 10 wherein said wall members are fabricated from two separate sheets of thermoplastic material which are sealed at their periphery.

12. The compartmented flexible intravenous container system as defined in claim 11 wherein said delaminated seal member is positioned away from said periphery of said first container body section in all directions.

13. The compartmented flexible intravenous container system as defined in claim 10 wherein said selective delaminated seal is formed by a partial parting of said second container sides so that fluid communication is effected with said first container body section prior to delamination.

14. The compartmented flexible intravenous container system as defined in claim 13 wherein said second container body section is secured to said internal wall surfaces of said first container body section adjacent said partial parting of said second container sides forming a portion of said delaminated seal.

* * * * *